(12) United States Patent
Mueller et al.

(10) Patent No.: US 7,198,799 B2
(45) Date of Patent: Apr. 3, 2007

(54) BIORESORBABLE NERVE GUIDE RAIL

(75) Inventors: Erhard Mueller, Stuttgart (DE); Helmut Hierlemann, Goeppingen (DE); Heinrich Planck, Nuertingen (DE); Burkhard Schlosshauer, Tuebingen (DE)

(73) Assignee: Deutsche Institute für Textil-und Faserforschung Stuttgart Stiftung des Oeffentlichen Rechts, Denkendorf (DE)

( * ) Notice: Subject to any disclaimer, the term of this patent is extended or adjusted under 35 U.S.C. 154(b) by 0 days.

(21) Appl. No.: 11/149,122

(22) Filed: Jun. 13, 2005

(65) Prior Publication Data

US 2006/0018947 A1 Jan. 26, 2006

Related U.S. Application Data

(63) Continuation-in-part of application No. 09/983,982, filed on Oct. 26, 2001, now abandoned.

(30) Foreign Application Priority Data

Oct. 28, 2000 (DE) ................. 100 53 611

(51) Int. Cl.
*A61F 2/04* (2006.01)
*C08G 63/02* (2006.01)

(52) U.S. Cl. ................. 424/426; 623/23.64; 623/23.75; 528/272

(58) Field of Classification Search ................. 424/426; 623/23.64, 23.75; 528/272
See application file for complete search history.

(56) References Cited

U.S. PATENT DOCUMENTS

| | | | |
|---|---|---|---|
| 4,617,271 A * | 10/1986 | Nambu | ........................ 435/182 |
| 5,358,475 A | 10/1994 | Mares et al. | |
| 5,656,605 A * | 8/1997 | Hansson et al. | ............... 514/21 |
| 5,834,029 A | 11/1998 | Bellamkonda et al. | |
| 5,908,783 A * | 6/1999 | Brewer | ........................ 435/368 |
| 5,925,053 A * | 7/1999 | Hadlock et al. | ............. 606/152 |
| 6,090,117 A * | 7/2000 | Shimizu | ...................... 606/152 |
| 6,676,675 B2 * | 1/2004 | Mallapragada et al. | ..... 606/152 |

FOREIGN PATENT DOCUMENTS

| | | |
|---|---|---|
| DE | 33 23 430 | 1/1985 |
| DE | 41 08 772 | 9/1992 |
| DE | 689 22 319 | 1/1996 |

(Continued)

OTHER PUBLICATIONS

Steuer et al., "Biohybride nerve guide for regeneration: degradable polylactide fibers coated with Schwann cells," Neurosci Lett 277:165-168, 1999.*

(Continued)

*Primary Examiner*—Jon Weber
*Assistant Examiner*—Rosanne Kosson
(74) *Attorney, Agent, or Firm*—Nath Law Group PLLC; Gary M. Nath; Tanya E. Harkins

(57) ABSTRACT

A biologically resorbable nerve guide rail with a microporous guide tube of polymers of hydroxycarboxylic acids, where the porosity allows a metabolism through the tube wall, but prevents the passage of cells, and optionally several monofilaments of polymers of hydroxycarboxylic acids located in the guide tube, is characterized in that the inner surface of the tube and/or the surface of the monofilaments have an orientation aid for longitudinally oriented colonization with Schwann's cells.

32 Claims, 1 Drawing Sheet

FOREIGN PATENT DOCUMENTS

| | | |
|---|---|---|
| DE | 196 41 334 | 4/1998 |
| DE | 197 36 449 | 2/1999 |
| JP | 04-262780 A | 9/1992 |
| JP | 04262780 A * | 9/1992 |
| JP | 04322657 | 11/1992 |
| JP | 04322657 A * | 11/1992 |

OTHER PUBLICATIONS

Molecular Cell biology 4th Ed., Lodish et al., eds., W. H. Freeman & Co., New York, 2000, pp. 912, 913 and 925.*

Steuer, H., et al., "Biohybride nerve guide for regeneration degradable polyactide fibers coated with rat Schwann cells." Neuroscience Letter, vol. 277, pp. 165-168, 1999.

Johnson, Alan R., "Contact Inhibition in the Failure of Mammalian CNS Axonal Regeneration." BioEssays, vol. 15, No. 12, pp. 807-813, Dec. 1993.

Dodd, Jane, et al., "Axon Guidance: A Compelling Case for Repelling Growth Cones." Cell, vol. 81, pp. 471-474, May 19, 1995.

Kolodkin, Alex K., "Growth cones and the cues that repel them." Trends Neurosci., vol. 19, pp. 507-513, 1996.

* cited by examiner

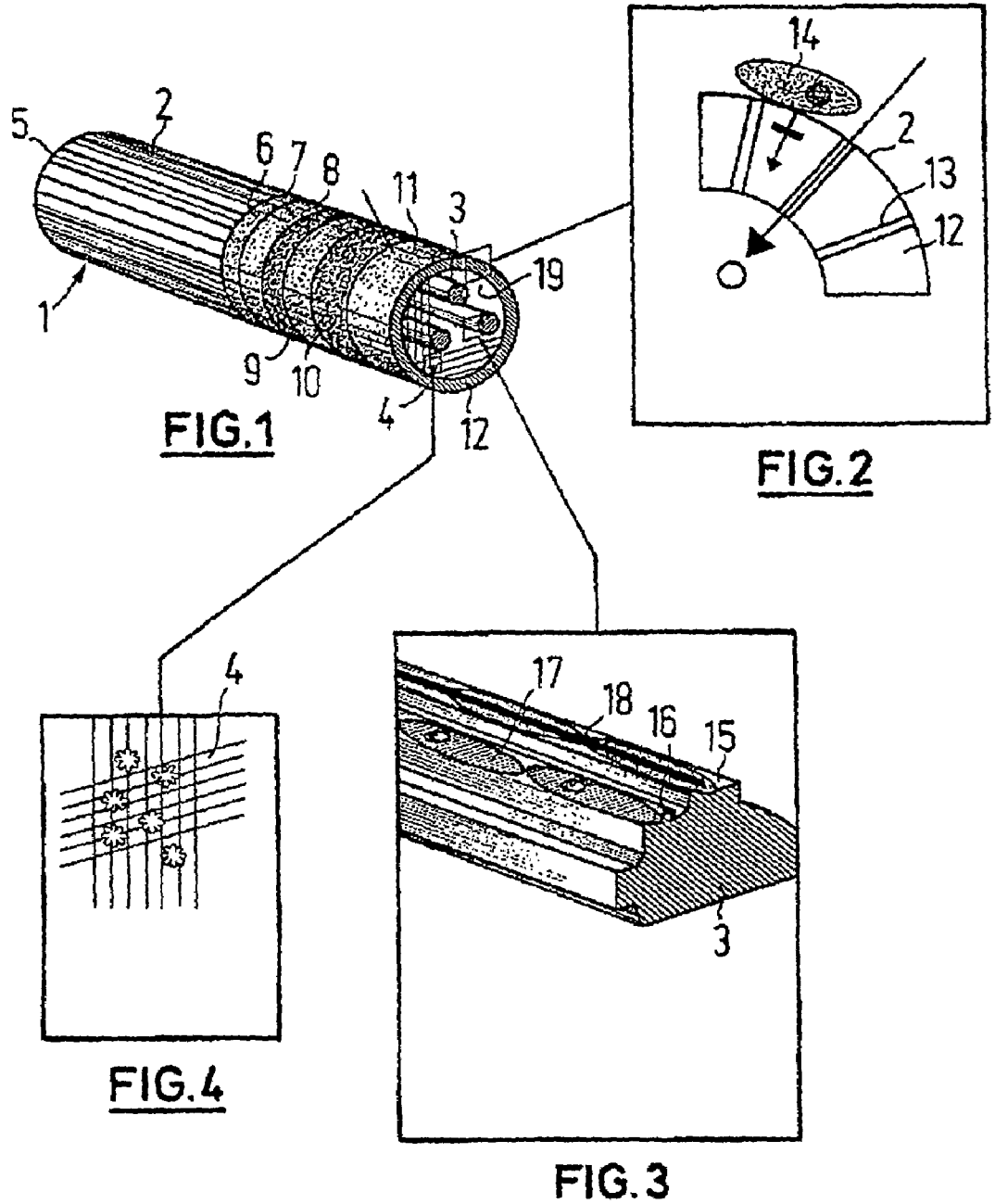

BIORESORBABLE NERVE GUIDE RAIL

This is a Continuation-in-part of U.S. application Ser. No. 09/983,982, filed Oct. 26, 2001 now abandoned, the entire contents of which is hereby incorporated by reference herein.

DESCRIPTION

The invention relates to a bioresorbable nerve guide rail having a microporous guide tube of polymers of hydroxycarboxylic acids, in which the porosity allows a metabolism through the tube wall, but prevents the passage of cells, and several filaments of polymers of hydroxycarboxylic acids located in the guide tube.

In the case of damage to nerve tracts in the central or peripheral nervous system, e.g. as a result of injury, the nerve cells are admittedly able to allow the growth of new axons, but generally they only find the other nerve end by chance or not at all. Thus, for bridging the defect in the nerve tract use is made of so-called nerve guide rails, which provide the axon with a directional orientation aid for growth.

It is already known to form such nerve guide rails from biodegradable material, particularly polymers of hydroxycarboxylic acids. Thus, when the nerve tract has regenerated, the nerve guide rail automatically dissolves, obviating the need for a second operation, which would otherwise be required to remove the nerve guide rail.

Normally a nerve has several parallel tracts, it has already been proposed to place monofilaments in the form of hollow microfibres in a biodegradable guide tube. However, hitherto the results have not been satisfactory.

Approaches in the treatment of damages in a nervous system are described in current scientific literature. A review article titled "Regenerating the damaged central nervous system" is given by Homer et al. in Nature 407 (2000), p. 963–970. A short review titled "Axon Guidance: A Compelling Case for Repelling Growth Cones" is given by Dodd et al. in Cell, Vol. 81 (1995), 471–474. Another review titled "Growth cones and the cues that repel them" is given by Kolodkin in TINS, Vol. 19 (1996), p. 507–513. Another review titled "Contact Inhibition in the Failure of Mammalian CNS Axonal Regeneration" is given by Johnson in BioEssays Vol. 15 (1993), p. 807–813. Therefore the problem of the invention is to provide a nerve guide rail, which accelerates a directional growth of operable nerve cells.

This problem is solved in that the inner surface of the guide tube and/or the surface of the monofilaments has an orientation aid for longitudinally oriented colonization with Schwann's or sheath cells.

Schwann's cells or their precursor cells aid the growth of axons through nerve guide rails and subsequently form an envelope or sheath around the axons which have grown. Schwann's cells have already been added to nerve guide rails to aid the growth of axons. The invention is based on the principle of allowing the Schwann's cells in longitudinal orientation to grow in joined manner along the guide tube and/or along the monofilaments, which brings about a forced longitudinal orientation of the axons, so that a faster joining of the nerve ends is brought about by a linear axon growth.

Due to the fact that the orientation aid is provided on the inside of the guide tube or on the outer surface of the monofilaments, during their growth the Schwann's cells and subsequently also the axons are linked with the interior of the guide tube, which can be supplied with the substances necessary for metabolism through the porosity of said guide tube.

The pore size of the porous wall or membrane of the guide tube is in the range 0.1 to 50 μm, preferably 0.5 to 3 μm. With such pore sizes nutrient media and the oxygen contained therein-can pass through the-guide tube wall. However, this also prevents the prejudicial growing in of connective tissue cells present outside the nerve guide rail.

The internal diameter of the tube is preferably in the range 0.5 to 10 mm, particularly 1 to 5 mm. This roughly corresponds to the thickness of naturally occurring nerves.

The production of the guide tube with the porous wall can take place in accordance with known membrane procedures. One possibility is the phase inversion or reversal method. For this purpose a solution of the biodegradable polymer can be extruded in tubular form in a bath, which is miscible with the solvent for the polymer, but which is not itself a solvent for the polymer. Another suitable membrane method is lyophilization. For this purpose a rod of suitable diameter and shape can be coated with a solution of the polymer and the latter can then be transformed into solid form by lyophilization and the pores form during drying.

The polymers can be homopolymers, copolymers and terpolymers of hydroxycarboxylic acids, carbonates or lactones, preference being given to copolymers and terpolymers. Suitable monomers are glycolide, lactide, particularly in the L or DL form, trimethyl carbonate (TMC), dioxanone, -hydroxybutyric acid and epsilon-caprolactone. Examples of suitable polymer materials are polyglycolide, polylactide, polycaprolactone, polytrimethylene carbonate, polydioxanone, polyhydroxybutyric acid, as well as copolymers, terpolymers or blends of these polymers.

The resorbability duration or its half-life can be adjusted through a suitable choice of the monomers and by correspondingly controlled quantity ratios. This applies both to the guide tube and to the monofilaments. As a rule the guide rail has disappeared within six months or has been dissolved to such an extent that a normal metabolism is possible.

Schwann's cells have the property of colonizing surfaces in monolayer form and grow on said surfaces. Thus, advantageously according to the invention the surface on which the Schwann's cells accumulate or are-attached, is longitudinally subdivided into narrow guide surfaces along which the Schwann's cells can be accumulated longitudinally in lancet-like manner. For this purpose the inner surface of the guide tube and/or the surface of the monofilaments are advantageously provided with longitudinal ribs and intermediate longitudinal grooves, so that both the longitudinal ribs and the longitudinal grooves can serve as narrow, axial guide surfaces for the Schwann's cells. The width of the ribs and/or grooves is preferably of the same order of magnitude as the width of a lancet-shaped Schwann's cell, so that there is a longitudinally directed joining together of the Schwann's cells in the form of a chain. The transitions between the longitudinal ribs and the intermediate valleys or longitudinal grooves are preferably given an angular construction as edges. Following the implantation of the guide rail, the axons can subsequently grow in a straight line along the chains of Schwann's cells. The width of the longitudinal ribs and preferably also the grooves is preferably between 5 and 30 μm. The depth of the grooves preferably does not exceed 10 μm and is in particular between 5 and 10 μm.

The inner surface of the guide tube and/or the surface of the monofilaments can advantageously be provided with a growing aid for a faster colonization of Schwann's cells. For this purpose are particularly suitable coatings with peptides or polypeptides, particular preference being given to polylysine. The polyamines or polypeptides to be used for coating with biologically active molecules can e.g. be derived from extracellular matrix proteins or enzymes. It is merely necessary to introduce a few Schwann's cells or precursor cells of said Schwann's cells into the nerve guide rail. They then propagate in the desired manner along the guide rail. It is also advantageous to hydrophilize the inner surface of the guide tube and/or the surface of the monofilaments. This can appropriately take place by a plasma treatment in the presence of oxygen, which leads to a better adhesion of the growing aid, particularly the peptides.

It is also possible and preferred if on the outside of the nerve guide rails are provided corresponding growing aids for connective tissue cells, particularly fibroblasts, in order to aid the growth of connective tissue around the nerve guide rail and in which following the resorption of the guide rail the nerve is embedded.

In a particularly preferred embodiment of the invention, which can also be provided independently of the orientation aid for the Schwann's cells, the nerve guide rail is constructed in such a way that the resorbability of the guide rail decreases over its length. Tests have shown that it is advantageous if at points where it has already grown again and where there has already been an enveloping of the axon with the Schwann's cells, the nerve is exposed as early as possible so as to permit a normal metabolism with the environment. At this time there is no longer any risk of a misorientation of the axon and external cells can also no longer inhibit growth. As axon growth takes place from the proximal nerve end, according to the invention the nerve guide rail is more rapidly resorbable at the proximal end than at the distal end. As hydrolytic degradation of the polymers of hydroxycarboxylic acids commences shortly after the implementation of the nerve guide rail, the different resorption duration of the nerve guide rail over its length is advantageously obtained by different polymers. This can be obtained through a different composition, i.e. via the use of different monomers or monomer ratios, as well as through different molecular weights.

The resorption time can increase continuously or discontinuously from the proximal to the distal end. A continuous increase can in particular be brought about in that the pre-formed guide tube and/or monofilaments are treated in different intensity with gamma rays as a function of their length. This can be achieved by different residence times. In a preferred production procedure the pre-formed parts of the guide rail can be placed in lead chambers, whose wall thickness increases from one end to the other, so that the radiation intensity decreases corresponding to the increase in the wall thickness.

Preference is given to a degradation time of 0.5 to 6 months along the length. The guide rail length is dependent on the size of the distance to be bridged and is normally between 1 and 10 cm.

However, it is also possible to obtain a different degradation duration over the guide rail length by the use of different polymers. It is known that lactide-containing polymers have a longer degradation period than glycolide-containing polymers. The degradation durations-can be controlled by corresponding copolymer or terpolymer percentages. For example the degradation time of epsilon-caprolactone-lactide polymer (50:50) is approximately one month and in the case of a corresponding copolymer with a monomer ratio of 90:10 three months. The degradation time is less than one month for an epsilon-caprolactone-trimethyl carbonate-glycolide polymer.

The thickness of the wall or membrane of the guide tube is advantageously 50 to 400 µm. Preferably the wall thickness is kept substantially constant considered over the length, so as not to impair metabolic processes through the porous wall as a result of excessive thicknesses thereof. Nevertheless, it is advantageously possible to control the different degradation duration by a different layer structure. Thus, the guide tube can be formed from several length-stepped layers, the lower, longest layer being formed from readily resorbable material and the following layers, which are correspondingly stepped shorter, have an increased degradation time. The bottom, rapidly resorbable layer on the multiply coated points is then protected by less resorbable covering layers, so that in this way there is a time-controlled, length-increasing resorption duration. Combinations of different compositions and irradiation are also possible.

The monofilaments can be constructed as hollow fibres, but they are preferably constructed as solid, compact fibres. This gives them the necessary stability and also facilitates the construction of the longitudinally structured surface as an orientation aid for the Schwann's cells.

The production of the monofilaments takes place with particular advantage by extrusion through correspondingly shaped dies with a roughly meander-shaped circumferential line. The setting of the increasing resorption duration from the proximal to the distal end advantageously takes place through the aforementioned irradiation. The monofilaments have a preferred diameter of 30 to 200 µm, particularly 100 to 150 µm.

The guide tube can contain many monofilaments, generally 10 to 1000, as a function of the guide tube size. However, the internal cross-section of the tube is not completely filled with monofilaments, because the cells on the one hand require space for growth and there is also a need for space for the nutrient medium within the tube. Normally the internal cross-section of the guide tube is roughly filled half to a third with monofilaments. With particular advantage both the inner surface of the guide tube and the surfaces of the monofilaments are intended for colonization by Schwann's cells and are provided with the corresponding orientation aids for the same.

In the guide rail, particularly in its resorbable material, can be incorporated active ingredients and/or growth factors, which at the latest are released during the biodegradation of the resorbable material. Thus, within the guide rail are advantageously incorporated acid-binding buffer substances. During the hydrolysis of the hydroxycarboxylic acid polymers fragments or monomers having carboxyl groups are formed. The thus possible undesired reduction of the pH-value can be absorbed by the buffers, which are preferably present in the resorbable polymers.

It is also possible to incorporate antibiotics, which in particular as a result of retarded release, prevent infections after implanting the guide rail.

The regeneration of lesioned nerves is typically compromised by various biological components which function as inhibitors of axonal growth. These inhibitors comprise extracellular matrix molecules such as distinct proteoglycans, cell membrane constituents such as Nogo and MAG, and soluble factors such as ephrins and semaphorins. Pharmaceutics that block the function of these inhibitors have the potential to support nerve regeneration. Thus, guide rails, which are provided for linking with the surrounding tissue, are advantageously provided at the ends which are to be connected to the surrounding tissue, with inhibitors for stop signals of the surrounding tissue. These stop signals normally prevent the growth of axons and the joining of exposed nerve ends of the spinal cord. These stop signals can have their stopping function inhibited by inhibitors such as antibodies or enzyme inhibitors.

The internal area of the guide tubes not taken up by the monofilaments and the initial colonization with Schwann's cells is preferably filled with a nutrient gel for Schwann's cells. It is preferably in the form of an aqueous gel, in which can be incorporated with particular advantage growth factors for the-Schwann's cells.

The nerve guide rails according to the invention preferably have a flexible construction, which is possible through a corresponding choice of the polymers, even without adding plasticizers. If desired, the nerve guide rails can also have branches. Tubular branches can e.g. be produced in that for shaping collapsible Y-shaped rods are coated, as is known in connection with vascular prostheses.

The production of the guide rails prepared for implantation preferably takes place in that the guide tube and monofilaments are separately prepared and the monofilaments are slid into the guide tube. Prior to sliding in, the monofilaments are preferably at least partly colonized with Schwann's cells or precursor cells.

Therefore the invention also relates to the monofilaments as such, finished with the orientation aid, particularly the longitudinal profiling, and optionally the growth aid for the Schwann's cells, in particular with the at least partial colonization with said cells or their precursors.

Further features of the invention can be gathered from the following description of a preferred embodiment of the invention in conjunction with the claims and the attached drawings, wherein show:

FIG. 1 A perspective view of a longitudinal portion of a nerve guide rail according to the invention.

FIG. 2 A partial cross-section through the porous membrane wall of the guide rail according to FIG. 1.

FIG. 3 A perspective partial view of a monofilament for the guide rail of FIG. 1.

FIG. 4 In symbolized form a gel matrix filling the interior of the guide tube.

In the embodiment shown in the drawings a guide rail 1 has a guide tube 2, in whose interior are longitudinally arranged approximately 10 to 50 monofilaments 3 (in the drawing only three are shown on a larger scale). The monofilaments 3 are embedded in a gel 4 (FIG. 4), which keeps them spaced.

The guide tube 2 is made from bioresorbable polymers of hydroxycarboxylic acids and has a structure in the form of several layers 5 to 11 of different length. They also differ in their composition, which is matched in such a way that the innermost layer 5 at the proximal end can be degraded fastest, namely within 0.5 months, whereas the outermost, shortest layer 11 is only degraded within 6 months. The degradation time of layers 6 to 10, which are shortened in stepped manner, is correspondingly in stepped rising form between the same.

This layer structure can in particular be achieved by a stepped immersion of a correspondingly pre-formed rod, particularly of PTFE (polytetrafluoroethylene) in polymer solutions of the different polymers, the rod for layer 5 being immersed deepest and for layers 6 to 11 increasingly less deep.

A porosity of the tube wall 12 constructed as a semipermeable membrane is obtained by lyophilization of the polymer solutions after immersion. The partial cross-section of FIG. 3 shows pores 13, which allow an exchange of nutrient medium and oxygen, but prevent the growing in of cells such as fibroblasts 14.

The monofilaments 3 are compact, i.e. having a solid construction and have a longitudinal profile of longitudinal ribs 15 and intermediate longitudinal grooves 16, which in each case roughly have the same width and which are present over the entire outer circumference of the monofilaments. The monofilaments are made from a polymer of hydroxycarboxylic acids having a resorption time in vivo of approximately six months. They are produced by extrusion from a correspondingly shaped die.

Through a stepped treatment with gamma rays, the resorption time is set in a substantially continuously decreasing form and at the proximal end like the layer 5 of guide tube 2 is only 0.5 month.

The surface of the monofilaments is coated with not shown polylysine, which aids the colonization with and growth of Schwann's cells 17 or their precursor cells. These cells are successively accumulated in lancet-shaped longitudinal orientation on the longitudinal ribs 15 and/or in the longitudinal groove 16 and in this way, after implantation, aid the regenerating growing in of an axon 18 of a nerve cell from the proximal nerve end along the chain of Schwann's cells shown in FIG. 3. The adhesion of the polylysine layer can be aided by prior plasma treatment of the monofilaments in the presence of oxygen, so that a hydrophilizing of the polymer surface takes place.

In the same way the inner surface 19 of the guide tube 2 is provided with longitudinal ribs and longitudinal grooves and coated with polylysine. There again, in the same way the Schwann's cells or their precursor cells are oriented. Thus, the nerve growth necessarily takes place along the guide rails in a plurality, but independent tracts.

The formation of the longitudinal ribs and longitudinal grooves on the inner surface 19 of the guide tube 2 can be brought about in that a corresponding rod, on which the guide tube is shaped, has a correspondingly structured surface.

In the gel 4 in the interior of the guide tube are incorporated growth factors aiding the proliferation of the Schwann's cells and optionally nutrients for said cells. In turn, the Schwann's cells give off factors, which activate axon growth and cause said axons to grow along the longitudinally oriented Schwann's cells. As axon growth starts from the proximal nerve end and there healing is terminated fastest, the support structure of the nerve guide rail, considered timewise, is initially no longer required at this end. Thus, this point can be degraded, particularly by hydrolytic degradation, after the Schwann's cells have been placed in the form of a jacket around the subsequently grown axons. With advancing axon growth the nerve guide rail loses its function and can be progressively and finally completely eliminated, which is achieved by the progressive resorption duration.

On the outer surface of the guide rail 1 is formed an envelope of fibroblasts 14, which take over the protective function of the guide tube. The growth of such cells can, in much the same way as for the monofilaments, be aided by hydrophilizing plasma treatment in the presence of oxygen and/or by peptide coating.

Prior to the sliding in of the monofilaments 3, the guide tube 2 can be filled with gel 4, e.g. a fibrin or collagen gel, the excess gel being displaced by the sliding in of the monofilaments. However, it is also possible to press in the gel together with the monofilaments or following the introduction of the latter. Preferably a colonization with Schwann's cells takes place prior to the introduction of the monofilaments into the guide tube. Further growth then takes place after joining together.

The Schwann's cells or their precursors are preferably taken from the patient beforehand. Since following nerve injury it is frequently necessary to wait for several weeks up to the resorption of the destroyed tissue, the time up to implantation is sufficient to culture the necessary quantity of Schwann's cells or their precursor cells.

The inventive subject matter being thus described, it will be obvious that the same may be modified or varied in many ways. Such modifications and variations are not to be regarded as a departure from the spirit and scope of the inventive subject matter, and all such modifications and variations are intended to be included within the scope of the following claims.

We claim:

1. A biologically resorbable nerve guide rail comprising:
   (a) a microporous guide tube of polymers of hydroxycarboxylic acids in the form of a tubular membrane, having pores sized between 0.1 and 50 microns and an inner tube diameter from 0.5 to 10 mm, the porosity permitting a metabolism through the tube wall, but preventing the passage of cells,
   (b) monofilaments of polymers of hydroxycarboxylic acids located in the guide tube, wherein the monofilaments are in the form of solid filaments having a diameter from 30 to 200 microns,
   and wherein at least one surface, selected from the group consisting of an inner surface of the tube and a surface of a monofilament, has an orientation aid in the form of longitudinal profiling,
   and wherein the resorbability of the guide rail decreases over its length and at a proximal end the guide rail is more rapidly resorbable than at a distal end.

2. The nerve guide rail of claim 1, wherein the pores are sized between 0.5 and 3.0 microns.

3. The nerve guide rail of claim 1, wherein the monofilaments have a diameter from 100 to 150 microns.

4. The guide rail according to claim 1, wherein the longitudinal profiling is formed by longitudinal ribs and intermediate longitudinal grooves.

5. The guide rail according to claim 1, wherein the at least on surface is a growth aid for Schwann's cells.

6. The guide rail according to claim 1, wherein at least the parts of the at least one surface of the guide tube to be colonized with Schwann's cells are hydrophilized.

7. The guide rail according to claim 6, wherein the parts of the at least one surface are hydrophilized by a plasma treatment in the presence of oxygen of the surface of the monofilaments.

8. The guide rail according to claim 1, wherein at least the parts of the at least one surface of the guide tube to be colonized with the Schwann's cells are at least partly colonized with Schwann's cells or their precursor cells.

9. The guide rail according to claim 1, wherein the monofilaments only fill part of the internal cross-section of the guide tube.

10. The guide rail according to claim 9, wherein a remaining part of the internal cross-section is filled with a stimulating aqueous nutrient gel for the Schwann's cells.

11. The guide rail according to claim 9, wherein approximately a third to a half of the internal cross-section of the guide tube is filled with monofilaments.

12. The guide rail according to claim 1, wherein at least one substance of the group consisting of active ingredients and growth factors is incorporated into the guide rail and will be released at the latest during biodegradation of the resorbable material.

13. The guide rail according to claim 12, wherein the at least one substance is incorporated into the resorbable material of at least one component of the guide rail consisting of the group of guide tube and monofilaments.

14. The guide rail according to claim 1, wherein acid-absorbing buffer substances are incorporated into the guide rail.

15. The guide rail according to claim 14, wherein the buffer substances are incorporated into the interior of the guide tube.

16. The guide rail according to claim 1, wherein inhibitors for stop signals of the surrounding tissue are incorporated in the ends of the guide rail provided for linking with the surrounding tissue.

17. A biologically resorbable nerve guide rail comprising:
   (a) a microporous guide tube of polymers of hydroxycarboxylic acids, having pores sized between 0.1 and 50 microns, the porosity permitting a metabolism through the tube wall, but preventing the passage of cells,
   monofilaments of polymers of hydroxycarboxylic acids located in the guide tube, wherein the resorbability of the guide rail decreases over its length and at a proximal end the guide rail is more rapidly resorbable than at a distal end.

18. The guide rail according to claim 17, wherein the monofilaments have a solid structure.

19. The guide rail according to claim 17, wherein the monofilaments only fill part of the internal cross-section of the guide tube.

20. The guide rail according to claim 19, wherein the remaining part of the internal cross-section is filled with a stimulating aqueous nutrient gel for the Schwann's cells.

21. The guide rail according to claim 17, wherein approximately a third to a half of the internal cross-section of the guide tube is filled with monofilaments.

22. The guide rail according to claim 17, wherein at least one substance of the group consisting of active substances and growth factors is incorporated into the guide rail and will be released at the latest during biodegradation of the resorbable material.

23. The guide rail according to claim 22, wherein the at least one substance is incorporated into the resorbable material of at least one component of the group consisting of guide rail and monofilaments.

24. The guide rail to claim 17, wherein acid-absorbing buffer substances are incorporated into the guide rail.

25. The guide rail according to claim 24, wherein the acid-absorbing buffer substances are incorporated into the interior of the guide tube.

26. The guide rail according to claim 17, wherein inhibitors for stop signals of the surrounding tissue are incorporated into ends of the guide rail provided for linking with the surrounding tissue.

27. A biologically resorbable nerve guide rail comprising:
   i. a microporous guide tube of polymers of hydroxycarboxylic acids in the form of a tubular membrane, having pores sized between 0.1 and 50 microns, the porosity permitting a metabolism through the tube wall, but preventing the passage of cells,
   ii. monofilaments of polymers of hydroxycarboxylic acids located in the guide tube, wherein the monofilaments are in the form of solid filaments having a diameter from 30 to 200 microns,
   and wherein at least one surface, selected from the group consisting of an inner surface of the tube and a surface of a monofilament, has an orientation aid in the form of longitudinal profiling, and wherein the resorbability of the guide rail decreases over its length and at a proximal end the guide rail is more rapidly resorbable than at a distal end.

28. A biologically resorbable nerve guide rail comprising:
i. a microporous guide tube of polymers of hydroxycarboxylic acids in the form of a tubular membrane, having pores sized between 0.1 and 50 microns, the porosity permitting a metabolism through the tube wall, but preventing the passage of cells,
ii. monofilaments of polymers of hydroxycarboxylic acids located in the guide tube, wherein the monofilaments are in the form of solid filaments having a diameter from 30 to 200 microns,
and wherein at least one surface, selected from the group consisting of an inner surface of the tube and a surface of a monofilament, has an orientation aid in the form of longitudinal profiling, wherein acid absorbing buffer substances are incorporated into the guide rail, and wherein the resorbability of the guide rail decreases over its length and at a proximal end the guide rail is more rapidly resorbable than at a distal end.

29. The biologically resorbable nerve guide rail of claim 1 wherein the inner surface of said guide tube has orientation aids in the form of longitudinal profiling.

30. A biologically resorbable nerve guide rail comprising:
i. a microporous guide tube of polymers of hydroxycarboxylic acids in the form of a tubular membrane, having pores sized between 0.1 and 50 microns, the porosity permitting a metabolism through the tube wall, but preventing the passage of cells,
ii. monofilaments of polymers of hydroxycarboxylic acids located in the guide tube, wherein the monofilaments are in the form of solid filaments having a diameter from 30 to 200 microns,
and wherein at least the surfaces of the monofilaments have orientation aids in the form of longitudinal profiling,
and wherein the resorbability of the guide rail decreases over its length.

31. A biologically resorbable nerve guide rail comprising:
i. a microporous guide tube of polymers of hydroxycarboxylic acids in the form of a tubular membrane, having pores sized between 0.1 and 50 microns, the porosity permitting a metabolism through the tube wall, but preventing the passage of cells,
ii. monofilaments of polymers of hydroxycarboxylic acids located in the guide tube, wherein the monofilaments are in the form of solid filaments having a diameter from 30 to 200 microns,
and wherein at least the surfaces of the monofilaments have orientation aids in the form of longitudinal profiling,
and wherein the number of monofilaments is 10 to 1000,
and wherein the resorbability of the guide rail decreases over its length and at a proximal end the guide rail is more rapidly resorbable than at a distal end.

32. The biologically resorbable nerve guide rail of claim 1 wherein a coating of a polylysine growth aid is applied to at least said monofilaments and optionally on the inner surface of said guide tube.

* * * * *